(12) United States Patent
Yamada et al.

(10) Patent No.: US 7,381,820 B2
(45) Date of Patent: Jun. 3, 2008

(54) α-1-PHOSPHORYLATED-2-DEOXY-2-FLUOROARABINOSIDE AND PROCESS FOR PRODUCING 2'-DEOXY-2'-FLUORO-β-D-ARABINONUCLEOSIDE

(75) Inventors: Kohei Yamada, Choshi (JP); Noritake Matsumoto, Habikino (JP); Hiroyuki Hayakawa, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 185 days.

(21) Appl. No.: 10/577,064

(22) PCT Filed: Oct. 22, 2004

(86) PCT No.: PCT/JP2004/015712

§ 371 (c)(1),
(2), (4) Date: Apr. 24, 2006

(87) PCT Pub. No.: WO2005/040181

PCT Pub. Date: May 6, 2005

(65) Prior Publication Data
US 2007/0135627 A1 Jun. 14, 2007

(30) Foreign Application Priority Data
Oct. 24, 2003 (JP) .............................. 2003-364013

(51) Int. Cl.
C07H 21/00 (2006.01)
A01N 43/04 (2006.01)
A61K 31/70 (2006.01)

(52) U.S. Cl. ............... 536/25.3; 536/25.33; 536/25.34; 514/43

(58) Field of Classification Search ..................... None
See application file for complete search history.

(56) References Cited
FOREIGN PATENT DOCUMENTS

| JP | 62-161797 | 7/1987 |
| JP | 63 258891 | 10/1988 |
| JP | 7 23395 | 3/1995 |
| JP | 2002-205996 | 7/2002 |
| JP | 2002 205996 | 7/2002 |
| WO | 99 67378 | 12/1999 |
| WO | 03/057895 | 7/2003 |

OTHER PUBLICATIONS

Lok et al., "Potent Gene-Specific Inhibitory Properties of Mixed-Backbone Antisense Oligonucleotides Comprised of 2'-Deoxy-2'-Fluoro-D-Arabinose and 2'-Deoxyribose Nucleotides", Biochemistry, vol. 41, pp. 3457-3467, 2002.
Min et al., "Oligonucleotides Comprised of Alternatiing 2'-Deoxy-2'-Fluoro-β-D-Arabinonucleosides and D-2'-Deoxyribonucleosides (2'F-ANA/DNA 'Altimers') Induce Efficient RNA Cleavage Mediated by RNASE H", Bioorganic & Medicinal Chemistry Letters, vol. 12, pp. 2651-2654, 2002.
Tann et al., "Fluorocarbohydrates in Synthesis. An Efficient Synthesis of 1-(2-Deoxy-2-Fluoro-β-D-Arabino-Furanosyl)-5-Iodouracil (β-FIAU) and 1-(2-Deoxy-2-Fluoro-β-D-Arabinofuranosyl)Thymine (β-FMAU)", J. Org. Chem., vol. 50, pp. 3644-3647, 1985.
Howell et al., "Antiviral Nucleosides. A Stereospecific, Total Synthesis of 2'-Fluoro-2'-Deoxy-β-D-Arabinofuranosyl Nucleosides", J. Org. Chem., vol. 53, pp. 85-88, 1988.
Wilds et al., "2'-Deoxy-2'-Fluoro-β-D-Arabinonucleosides and Oligonucleotides (2'F-ANA):Synthesis and Physicochemical Studies", Nucleic Acids Research, vol. 28, No. 18, pp. 3625-3635, 2000.
Elzagheid et al., "A New Synthesis of 9-(2-Deoxy-2-Fluoro-β-D-Arabinofuranosyl) Guanine (ARAF-G)", Nucleosides, Nucleotides & Nucleic Acids, vol. 22, No. 5-8, pp. 1339-1342, 2003.
Yamada et al., "Practical Synthesis of 2'-Deoxy-2'-Fluoroarabinofuranosyl Purine Nucleosides by Chemo-Emzymatic Method", Nucleic Acids Symposium Series, vol. 48, pp. 45-46, 2004.

Primary Examiner—Patrick Lewis
(74) Attorney, Agent, or Firm—Oblon, Spivak, McClelland, Maier & Neustadt, P.C.

(57) ABSTRACT

A method for producing 2'-deoxy-2'-fluoro-β-D-arabinonucleoside represented by formula (II):

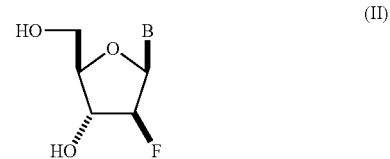

(II)

(wherein B represents a base), in particular, 2'-deoxy-2'-fluoro-β-D-arabinopurinenucleoside, which method comprises causing a nucleoside phosphorylase to act on α-1-phosphorylated-2-deoxy-2-fluoroarabinoside represented by formula (I):

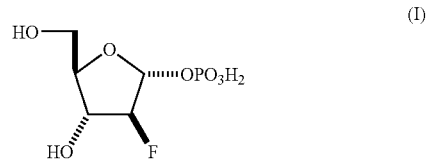

(I)

or a mixture of α- and β-isomers of 1-phosphorylated-2-deoxy-2-fluoroarabinoside represented by formula (V'):

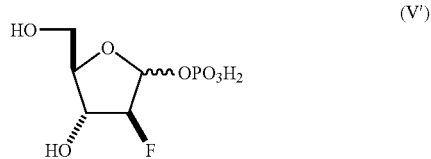

(V')

and on a base. The compound can be produced at high yield and in a convenient and highly stereoselective manner.

13 Claims, No Drawings

α-1-PHOSPHORYLATED-2-DEOXY-2-FLUOROARABINOSIDE AND PROCESS FOR PRODUCING 2'-DEOXY-2'-FLUORO-β-D-ARABINONUCLEOSIDE

TECHNICAL FIELD

The present invention relates to α-1-phosphorylated-2-deoxy-2-fluoroarabinoside, and to a method for producing 2'-deoxy-2'-fluoro-β-D-arabinonucleoside, which employs the phosphorylated fluoroarabinoside as a key intermediate.

BACKGROUND ART

In recent years, by virtue of its biological activity, an antisense oligonucleotide containing, as a constituent, 2'-deoxy-2'-fluoro-β-D-arabinonucleoside (2'F-ANA) has become more attractive (Patent Document 1 and Non-Patent Documents 1 and 2).

2'F-ANA is a known compound, and methods for chemically synthesizing the compound have already been reported (Patent Document 2 and Non-Patent Documents 3 and 4). Specifically, since 2'F-ANA is difficult to derive from natural nucleosides, 2'F-ANA is synthesized through substitution reaction (condensation reaction) between a 1-halogenated sugar derivative and a base of nucleic acid. However, the resultant reaction mixture contains the α-isomer of the arabinonucleoside in addition to the β-isomer thereof, and thus production of highly pure 2'F-ANA requires a purification process employing, for example, an intricate column chromatography.

Of species of 2'F-ANA, 2'-deoxy-2'-fluoro-β-D-arabinopyrimidinenucleoside can be synthesized relatively easily. In contrast, no efficient method for synthesizing 2'-deoxy-2'-fluoro-β-D-arabinopurinenucleoside has yet been established, since the reaction mixture contains a variety of isomers (e.g., α-isomer, β-isomer, 7-substituted isomer, and 9-substituted isomer).

Enzymatic synthesis methods have been proposed as one means for overcoming drawbacks involved in the aforementioned chemical synthesis methods. For example, there has been proposed a method in which an α-1-phosphorylated sugar derivative is synthesized by shifting the isomerization equilibrium of 1-phosphorylated-2-deoxyribose products, followed by employment of a nucleoside phosphorylase, to thereby produce a target nucleoside (Patent Document 3).

However, the present inventors have found that 1-phosphorylated-2-deoxy-2-fluoroarabinoside is relatively stable, and the equilibrium of the α-isomer and β-isomer of the fluoroarabinoside is difficult to shift to one direction, and therefore difficulty is encountered in applying the aforementioned enzymatic synthesis method to production of 2'F-ANA.

Also, there has been reported a method for enzymatically synthesizing 2'-deoxy-2'-fluoro-β-D-arabinopurinenucleoside from 2'-deoxy-2'-fluoro-β-D-arabinopyrimidinenucleoside and a purine base by use of a nucleoside phosphorylase (Patent Document 4).

Patent Document 1: WO99/67378 pamphlet
Patent Document 2: JP-B-H7-23395
Patent Document 3: JP-A-2002-205996
Patent Document 4: JP-A-S63-258891
Non-Patent Document 1: Biochemistry, 41, 3457 (2002)
Non-Patent Document 2: Bioorg. Med. Chem. Lett., 12, 2651, (2002)
Non-Patent Document 3: J. Org. Chem., 50, 3644 (1985)
Non-Patent Document 4: J. Org. Chem., 53, 85 (1988)

DISCLOSURE OF THE INVENTION

Problems to be Solved by the Invention

However, the aforementioned enzymatic synthesis method is not necessarily satisfactory for the following reasons;
(i) chemically synthesized, expensive 2'-deoxy-2'-fluoro-β-D-arabinopyrimidinenucleoside is employed as a raw material; (
ii) 2'-deoxy-2'-fluoro-β-D-arabinopurinenucleoside (i.e., a target product) is synthesized at a very low yield (less than 15% on the basis of the purine base); and (iii) two types of nucleoside phosphorylases must be employed, etc. Such a low yield in the aforementioned method is considered to be caused by low reaction efficiency in phosphorolysis of 2'-deoxy-2'-fluoro-β-D-arabinopyrimidinenucleoside by means of the nucleoside phosphorylases.

Accordingly, an object of the present invention is to provide a method for producing, at high yield and in a convenient and highly stereoselective manner, 2'F-ANA; in particular, 2'-deoxy-2'-fluoro-β-D-arabinopurinenucleoside, which has been difficult to stereoselectively synthesize at high yield. Particularly, an object of the present invention is to provide a method for producing, at high purity, on an industrial scale, and in a convenient manner, 9-(2-fluoro-β-D-arabinosyl)guanine, which has conventionally been very difficult to synthesize.

Means for Solving the Problems

In view of the foregoing, the present inventors have conducted extensive studies, and as a result have found that (i) 1-phosphorylated-2-deoxy-2-fluoroarabinoside is unexpectedly stable in an aqueous solution, and the a-isomer of the fluoroarabinoside is fully available as a substrate for nucleoside phosphorylase; (ii) α-1-phosphorylated-2-deoxy-2-fluoroarabinoside is stereoselectively produced through hydrolysis and phosphorylation of a 2-deoxy-2-fluoroarabinose derivative represented by formula (III); (iii) phosphorylation of a compound represented by formula (III) in the presence of a strong base acid salt produces a mixture of α- and β-isomers of 1-phosphorylated-2-deoxy-2-fluoroarabinoside, in which the proportion of the α-isomer, which serves as a substrate for nucleoside phosphorylase, is higher than that of β-1-phosphorylated-2-deoxy-2-fluoroarabinoside, which does not serve as a substrate for the enzyme; and (iv) 2'-deoxy-2'-fluoro-β-D-arabinonucleoside is produced at high yield without employment of two types of nucleoside phosphorylases, when the raw material to be employed is 1-phosphorylated-2-deoxy-2-fluoroarabinoside (α-isomer or a mixture of α- and (β-isomers) instead of 2'-deoxy-2'-fluoro-β-D-arabinopyrimidinenucleoside. The present invention has been accomplished on the basis of these findings.

to

Accordingly, the present invention provides α-1-phosphorylated-2-deoxy-2-fluoroarabinoside represented by formula (I):

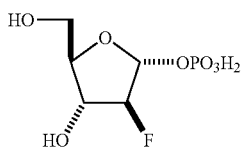

or a salt thereof.

The present invention also provides a method for stereoselectively producing α-1-phosphorylated-2-deoxy-2-fluoroarabinoside represented by formula (I):

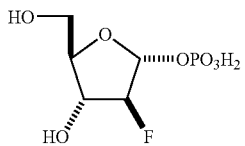

which method comprises hydrolyzing a 2-deoxy-2-fluoroarabinose derivative represented by formula (III):

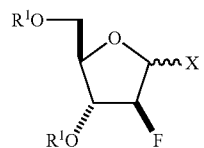

(wherein $R^1$ represents a hydroxyl-protective group, and X represents a leaving group), thereby stereoselectively yielding an α-1-hydroxyl isomer represented by formula (IV):

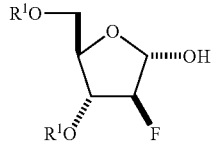

(wherein $R^1$ has the same meaning as defined above); phosphorylating the compound of formula (IV), thereby forming an α-1-phosphorylated-2-deoxy-2-fluoroarabinoside derivative represented by formula (V):

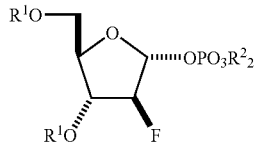

(wherein $R^1$ has the same meaning as defined above, and $R^2$ represents a hydrogen atom or a phosphate-protective group); and subsequently removing the hydroxyl-protective group(s) and/or the phosphate-protective group(s).

The present invention also provides a method for producing a mixture of α- and β-isomers of 1-phosphorylated-2-deoxy-2-fluoroarabinoside represented by formula (V'):

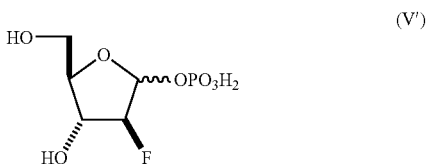

which method comprises phosphorylating, in the presence of a strong acid salt, a 2-deoxy-2-fluoroarabinose derivative represented by formula (III):

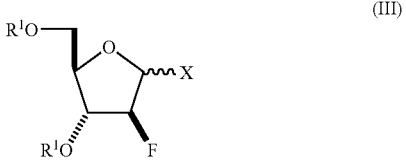

(wherein $R^1$ represents a hydroxyl-protective group, and X represents a leaving group), thereby yielding a mixture of α- and β-isomers of a 1-phosphorylated-2-deoxy-2-fluoroarabinoside derivative represented by formula (V):

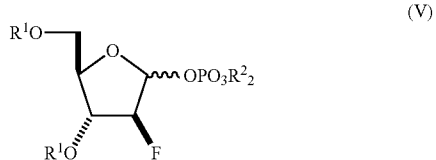

(wherein $R^1$ has the same meaning as defined above, and $R^2$ represents a hydrogen atom or a phosphate-protective group); and subsequently removing the hydroxyl-protective group(s) and/or the phosphate-protective group(s).

to

The present invention also provides a method for producing 2'-deoxy-2'-fluoro-β-D-arabinonucleoside represented by formula (II):

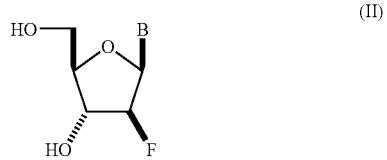

(wherein B represents a base), which method comprises by comprising causing a nucleoside phosphorylase to act on α-1-phosphorylated-2-deoxy-2-fluoroarabinoside represented by formula (I):

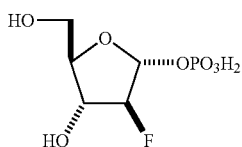

or a mixture of α- and β-isomers of 1-phosphorylated-2-deoxy-2-fluoroarabinoside represented by formula (V'):

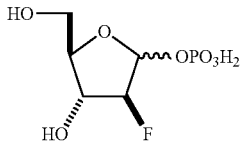

and on a base.

The present invention also provides a method for producing 9-(2-fluoro-β-D-arabinosyl)guanine represented by formula (VII):

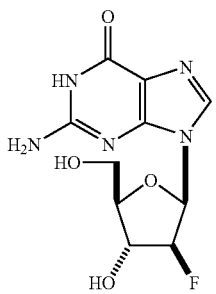

which method comprises causing a nucleoside phosphorylase to act on α-1-phosphorylated-2-deoxy-2-fluoroarabinoside represented by formula (I):

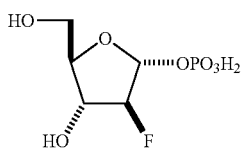

or a mixture of α- and β-isomers of 1-phosphorylated-2-deoxy-2-fluoroarabinoside represented by formula (V'):

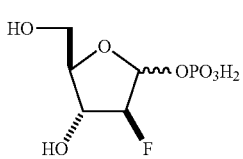

and on a 2-amino-6-substituted purine, thereby yielding 2-amino-6-substituted-9-(2-fluoro-β-D-arabinosyl)purine represented by formula (VI):

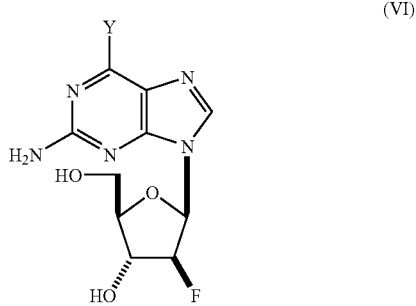

(wherein Y represents a substituent); and treating the thus-obtained purine nucleoside with a hydrolase.

The present invention also provides a method for producing 9-(2-fluoro-β-D-arabinosyl)guanine represented by formula (VII):

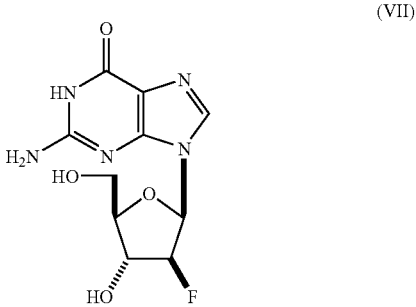

which method comprises causing a nucleoside phosphorylase and a nucleosidase to act on α-1-phosphorylated-2-deoxy-2-fluoroarabinoside represented by formula (I):

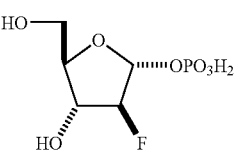

or a mixture of α- and β-isomers of 1-phosphorylated-2-deoxy-2-fluoroarabinoside represented by formula (V'):

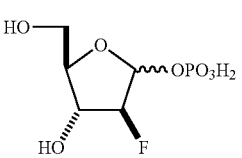

and on guanosine 5'-monophosphate.

Effects of the Invention

According to the present invention, 2'F-ANA; in particular, 2'-deoxy-2'-fluoro-β-D-arabinopurinenucleoside, which has conventionally been difficult to stereoselectively synthesize at high yield, can be produced at high yield and in a convenient and highly stereoselective manner. Particularly, according to the present invention, 9-(2-fluoro-β-D-arabinosyl)guanine, which has conventionally been very difficult to synthesize, can be produced at high yield, on an industrial scale, and in a convenient and highly stereoselective manner.

Therefore, the α-1-phosphorylated-2-deoxy-2-fluoroarabinoside of the present invention or a salt thereof, and the production method of the present invention employing this compound as a key intermediate are useful for industrial production of antisense drugs.

BEST MODE FOR CARRYING OUT THE INVENTION

No particular limitation is imposed on the salt of the compound represented by formula (I) (i.e., compound (I)). Examples of the salt include alkali metal salts (e.g., sodium salt and potassium salt); alkaline earth metal salts (e.g., calcium salt and magnesium salt); organic base salts (e.g., trimethylamine salt, triethylamine salt, pyridine salt, picoline salt, and dicyclohexylamine salt); and ammonium salts. A sodium salt is preferred.

Next will be described typical methods for producing the compound (I).

Synthesis Method 1 (α-isomer):

The substituent at 1-position of a compound (III) is hydrolyzed to yield the (α-isomer of a compound (IV) in a stereoselective manner; the hydroxyl group at 1-position of the compound (IV) is phosphorylated to form a compound (V); and removal of the hydroxyl-protective group(s) and/or the phosphate-protective group(s) of the compound (V) is performed.

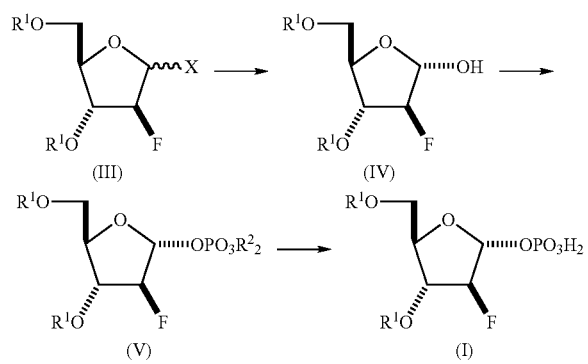

(In the above reaction scheme, $R^1$ represents a hydroxyl-protective group, X represents a leaving group, and $R^2$ represents a hydrogen atom or a phosphate-protective group.)

Examples of the hydroxyl-protective group represented by $R^1$ in formulas (III) to (V) include C1-C10 acyl groups such as formyl, acetyl, pivaloyl, and benzoyl; C7-C20 aralkyl groups such as benzyl and p-methoxybenzyl; and C1-C20 alkylsilyl groups such as t-butyldimethylsilyl and t-butyldiphenylsilyl. Of these, a C1-C10 acyl group is preferred, with a benzoyl group being particularly preferred.

Examples of the leaving group represented by X include halogen atoms such as chlorine, bromine, and iodine; a mesyl group; a tosyl group; a trifluoromethanesulfonyl group; and C1-C10 acyl groups such as formyl, acetyl, pivaloyl, and benzoyl. A halogen atom is preferred, with a bromine atom being particularly preferred.

Examples of the phosphate-protective group represented by $R^2$ include an allyl group, and an alkyl group which may have a substituent. Examples of alkyl groups include C1-C10 alkyl groups such as methyl, ethyl, n-propyl, isopropyl, n-butyl, isobutyl, and t-butyl. Examples of the substituent of such an alkyl group include a cyano group, a trimethylsilyl group, and a phenyl group. Examples of substituted alkyl groups include a 2-cyanoethyl group, 2-trimethylsilylethyl group, and a benzyl group.

The compound (III) can be synthesized through a known method (J. Org. Chem., 50, 3644 (1985), J. Org. Chem., 53, 85 (1988), or JP-B-H7-23395).

Hydrolysis reaction at 1-position of the compound (III) may be performed in an organic solvent such as acetonitrile, N,N-dimethylformamide (DMF), methanol, or tetrahydrofuran (THF) in the presence of a base such as tributylamine or triethylamine, such that each of the amounts of the base and water to be employed is 1 mol or more on the basis of 1 mol of the compound (III). The reaction temperature is preferably 0 to 100° C., and the reaction time is preferably about 1 to about 24 hours. If desired, the reaction may be performed with stirring.

If desired, the thus-obtained compound (IV) may be purified through generally employed sugar purification means (e.g., partition by means of an organic solvent, or a variety of chromatography treatments), and the thus-purified compound may be subjected to subsequent phosphorylation reaction.

Phosphorylation reaction of the substituent at 1-position of the compound (IV) can be performed through a known method. Examples of such a known method include a phosphorylation method employing a pentavalent phosphorylating agent; and a method including phosphite formation employing a trivalent phosphorylating agent, and subsequent oxidation.

In the method employing a pentavalent phosphorylating agent, specifically, 1 to 10 mol of a phosphorylating agent (e.g., phosphorus oxychloride, monoalkylphosphoryl halide, or dialkylphosphoryl halide) may be employed on the basis of 1 mol of the compound (IV) in an organic solvent such as acetonitrile, THF, or dichloromethane in the presence of a base such as tributylamine, triethylamine, or pyridine. The reaction temperature is preferably −78 to 120° C., and the reaction time is preferably about 1 to about 24 hours.

In the method employing a trivalent phosphorylating agent, specifically, the compound (IV) may be reacted with a phosphite-forming agent (e.g., phosphorus trichloride or chlorophosphorodiamidite) in an organic solvent such as acetonitrile, THF, dichloromethane, or 1,4-dioxane in the presence of a base such as tributylamine, triethylamine, or pyridine, and subsequently reacted with an alcohol such as cyanoethanol or allyl alcohol to thereby form a phosphite, followed by oxidation of the phosphite with an oxidizing agent such as m-chloroperbenzoic acid, t-butyl peroxide, or hydrogen peroxide. The amount of the phosphorylating agent, alcohol, or oxidizing agent to be employed may be 1 to 10 mol on the basis of 1 mol of the compound (IV). The reaction temperature is preferably −78 to 120° C., and the reaction time is preferably about 1 to about 24 hours.

If desired, the thus-obtained compound (V) is purified through generally employed sugar-purification means (e.g., partition by means of an organic solvent, or a variety of chromatography treatments), and the thus-purified compound is subjected to subsequent deprotection reaction.

Removal of the hydroxyl-protective group(s) and/or phosphate-protective group(s) of the compound (V) may be performed through a generally employed technique (e.g., acid treatment, alkali treatment, catalytic reduction, or treatment with ammonium fluoride), which is appropriately selected in accordance with the employed protective group(s).

If desired, the compound (I) produced through the above-described procedure is purified through generally employed sugar purification means (e.g., partition by means of an organic solvent, a variety of chromatography treatments, or crystallization), and the thus-purified compound is subjected to subsequent enzymatic reaction.

Synthesis Method 2 (Mixture of α- and β-isomers):

A compound (III) can be treated with a phosphorylating agent in the presence of a strong acid salt, to thereby form a mixture of α- and β-isomers (V), which is a protected product (hereinafter the mixture may be referred to as an "αβ-isomers mixture").

In the phosphorylation reaction, 1 mol or more of a phosphoric acid derivative (e.g., orthophosphoric acid, a phosphoric acid monoester, or a phosphoric acid diester) may be reacted with 1 mol of the compound (III) in an organic solvent such as acetonitrile, dichloromethane, DMF, or methyl ethyl ketone in the presence of a base such as tributylamine or triethylamine. The reaction temperature is preferably −78 to 120° C., and the reaction time is preferably about 1 to about 24 hours.

During the phosphorylation, a strong acid salt, particularly preferably a strong acid salt which generates a halide ion or a nitrate ion (about 0.1 to about 20 mol) is added to 1 mol of the compound (III). As shown in Table 1, addition of such a strong acid salt enables the α-isomer to be synthesized preferentially to the β-isomer.

Examples of the strong acid salt which generates a halide ion or a nitrate ion include metal halides and ammonium halides, such as tetra-n-butylammonium iodide, tetraethylammonium iodide, tetra-n-butylammonium bromide, tetraethylammonium bromide, tetra-n-butylammonium chloride, and tetraethylammonium chloride; and metal nitrates and ammonium nitrates, such as tetra-n-butylammonium nitrate. Of these, tetra-n-butylammonium iodide, tetra-n-butylammonium bromide, tetra-n-butylammonium chloride, tetraethylammonium chloride, and tetra-n-butylammonium nitrate are preferred.

If desired, the thus-obtained compound (V) is purified through generally employed sugar purification means (e.g., partition by means of an organic solvent, or a variety of chromatography treatments), and the thus-purified compound is subjected to subsequent deprotection reaction.

Removal of the hydroxyl-protective group(s) and/or phosphate-protective group(s) of the compound (V) produces an αβ-isomers mixture (V'):

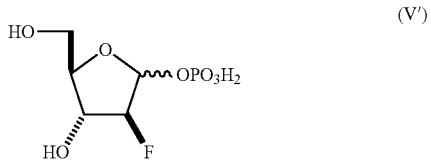

which contains the compound (I) and the β-isomer thereof. In the αβ-isomers mixture (V'), the α/β ratio is 1.9 to 2.6. Removal of the protective group(s) may be performed through a generally employed technique (e.g., acid treatment, alkali treatment, catalytic reduction, or treatment with ammonium fluoride), which is appropriately selected in accordance with the employed protective group(s).

If desired, the αβ-isomers mixture produced through the above-described procedure is purified through generally employed sugar purification means (e.g., partition by means of an organic solvent, a variety of chromatography treatments, or crystallization), and the thus-purified mixture is subjected to subsequent enzymatic reaction.

Next will be described a method for producing a 2'F-ANA represented by formula (II) by causing a nucleoside phosphorylase to act on the compound (I) or the αβ-isomers mixture (V') and on a base (B).

No particular limitation is imposed on the nucleoside phosphorylase to be employed for reaction, so long as it enables a compound (II) to be synthesized. However, purine nucleoside phosphorylase is particularly preferred. Such a nucleoside phosphorylase per se and methods for preparation thereof are known, and the phosphorylase can be easily prepared through such a known method. Specifically, no particular limitation is imposed on the source from which such a nucleoside phosphorylase is derived, and the nucleoside phosphorylase to be employed may be derived from any source, for example, an animal, a plant, or a microorganism. From the viewpoint of, for example, convenience of preparation, the nucleoside phosphorylase is preferably derived from a microorganism. In the case where a nucleoside phosphorylase gene to be employed has been cloned, the cloned nucleoside phosphorylase gene may be integrated into a host (e.g., *Escherichia coli*) through a customary method, to thereby mass-produce the enzyme, and the enzyme may be prepared from the transformation.

The nucleoside phosphorylase may be prepared in any form, so long as the preparation form exhibits the activity of the enzyme. Specific examples of the preparation form include a microbial cell, a product obtained through treatment of the microbial cell, and an enzyme preparation obtained from the product.

Microbial cell preparation can be performed by culturing of a microorganism, through a customary method, in a medium in which the microorganism can be grown, followed by collection of the resultant microbial cells through centrifugation or a similar technique. Specifically, microbial cell preparation will now be described by taking, as an example, the case where a bacterium belonging to the genus *Bacillus* or *Escherichia* is employed. In such a case, the medium which may be employed is, for example, a bouillon medium, an LB medium (1% tryptone, 0.5% yeast extract, 1% sodium chloride), or a 2xYT medium (1.6% tryptone, 1% yeast extract, 0.5% sodium chloride). Microbial cells exhibiting nucleoside phosphorylase activity can be prepared by inoculating the inoculum into such a medium as described above, followed by culturing at about 30 to about 50° C. for about 10 to about 50 hours with, if necessary, stirring; and subjecting the resultant culture broth to centrifugation for collection of microbial cells.

The microbial-cell-treated product may be a microbial-cell-disrupted product or a microbial-cell-wall-denatured (or microbial-cell-membrane-denatured) product, which is obtained through treatment of the aforementioned microbial cells with a generally employed treatment technique, such as mechanical disruption (by means of, for example, a Waring blender, a French press, a homogenizer, or a mortar), freezing and thawing, autolysis, drying (by means of, for example, freeze-drying or air-drying), enzymatic treatment (by means of, for example, lysozyme), ultrasonic treatment, or chemical treatment (by means of, for example, an acid or an alkali).

The enzyme preparation may be a crude or purified enzyme preparation, which is obtained by subjecting nucleoside-phosphorylase-activity-exhibiting fractions of the aforementioned microbial-cell-treated product to generally employed enzyme purification means, such as salting-out treatment, isoelectric precipitation treatment, precipitation treatment with an organic solvent, dialysis treatment, or a variety of chromatography treatments.

The base (B) to be added to the reaction mixture, which is selected in accordance with the intended synthesis, may be, for example, a commercially available base or a base prepared through a known method.

The base (B) is preferably a purine base or a derivative thereof. Examples of the purine base derivative include derivatives having a substituent selected from among a halogen atom, an alkyl group, a haloalkyl group, an alkenyl group, a haloalkenyl group, an alkynyl group, an amino group, an alkylamino group, a hydroxyl group, a hydroxyamino group, an aminooxy group, an alkoxy group, a mercapto group, an alkylmercapto group, an aryl group, an aryloxy group, and a cyano group. No particular limitation is imposed on the number and position of such a substituent.

Examples of the halogen atom include chlorine, fluorine, iodine, and bromine.

Examples of the alkyl group include C1-C6 alkyl groups such as methyl, ethyl, and n-propyl.

The haloalkyl group may be any of the aforementioned C1-C6 alkyl groups substituted with any of the aforementioned halogen atoms. Specific examples of the haloalkyl group include fluoromethyl, difluoromethyl, trifluoromethyl, bromomethyl, and bromoethyl.

Examples of the alkenyl group include C2-C7 alkenyl groups such as vinyl and allyl.

Examples of the haloalkenyl group include C2-C7 alkenyl groups substituted with any of the aforementioned halogen atoms, such as bromovinyl and chlorovinyl.

Examples of the alkynyl group include C2-C7 alkynyl groups such as ethynyl and propynyl.

Examples of the alkylamino group include amino groups substituted with any of the aforementioned C1-C6 alkyl groups, such as methylamino, ethylamino, diethylamino, and diethylamino.

Examples of the aryloxy group include those having any of the aforementioned aryl groups. Specific examples include a phenoxy group; alkyiphenoxy groups having any of the aforementioned C1-C6 alkyl groups, such as methylphenoxy and ethylphenoxy; alkoxyphenoxy groups having any of the aforementioned C1-C6 alkoxy groups, such as methoxyphenoxy and ethoxyphenoxy; alkylaminophenoxy groups having any of the aforementioned C1-C6 alkylamino groups, such as dimethylaminophenoxy and diethylaminophenoxy; and halogenophenoxy groups having any of the aforementioned halogen atoms, such as chlorophenyloxy and bromophenyloxy.

Examples of the purine base and derivatives thereof include purine, 6-aminopurine (adenine), 6-hydroxypurine (hypoxanthine), 6-fluoropurine, 6-chloropurine, 6-methylaminopurine, 6-dimethylaminopurine, 6-trifluoromethylaminopurine, 6-benzoylaminopurine, 6-acetylaminopurine, 6-hydroxyaminopurine, 6-aminooxypurine, 6-methoxypurine, 6-acetoxypurine, 6-benzoyloxypurine, 6-methylpurine, 6-ethylpurine, 6-trifluoromethylpurine, 6-phenylpurine, 6-mercaptopurine, 6-methylmercaptopurine, 6-aminopurine-1-oxide, 6-hydroxypurine-1-oxide, 2-amino-6-hydroxypurine (guanine), 2,6-diaminopurine, 2-amino-6-chloropurine, 2-amino-6-iodopurine, 2-aminopurine, 2-amino-6-mercaptopurine, 2-amino-6-methylmercaptopurine, 2-amino-6-hydroxyaminopurine, 2-amino-6-methoxypurine, 2-amino-6-benzoyloxypurine, 2-amino-6-acetoxypurine, 2-amino-6-methylpurine, 2-amino-6-cyclopropylaminomethylpurine, 2-amino-6-phenylpurine, 2-amino-8-bromopurine, 6-cyanopurine, 6-amino-2-chloropurine (2-chloroadenine), 6-amino-2-fluoropurine (2-fluoroadenine), 6-amino-3-deazapurine, 6-amino-8-azapurine, 2-amino-6-hydroxy-8-azapurine, 6-amino-7-deazapurine, 6-amino-1-deazapurine, and 6-amino-2-azapurine.

2'F-ANA can be synthesized by adding a nucleoside phosphorylase (about 5 units/mL or more, preferably about 50 units/mL or more) to the compound (I) or the αβ-isomers mixture (V') and to the base (B) in a buffer solution (e.g., a Tris-HCl buffer solution or a phosphate buffer solution). The amount of the compound (I) or αβ-isomers mixture (V') to be employed is preferably about 1 to about 200 mM, particularly preferably 10 to 100 mM. The base (B) to be employed is preferably 1 equivalent or more, particularly preferably about 2 to about 5 equivalents (by mole), with respect to the compound (I). The reaction temperature is preferably 20 to 70° C., particularly preferably 40 to 60° C. The reaction time is preferably about 1 to about 100 hours. If desired, the reaction may be performed with stirring.

Next will be specifically described production of 9-(2-fluoro-β-D-arabinosyl)guanine (i.e., compound (VII)) through the above-described production method.

The compound (VII) can be produced as follows. A nucleoside phosphorylase similar to that described above is added to the compound (I) or the αβ-isomers mixture (V') and to a 2-amino-6-substituted-purine, to thereby yield a compound (VI), and the compound (VI) is treated with a hydrolase.

No particular limitation is imposed on the 2-amino-6-substituted-purine to be employed for the reaction, so long as the 2-amino-6-substituted-purine, which is a purine derivative, has a hydrolyzable substituent Y. Examples of the substituent Y include halogen atoms (e.g., chlorine, bromine, and iodine), an amino group, a hydroxy group, a mercapto group, a methylmercapto group, a hydroxyamino group, a methoxy group, a benzoyloxy group, and an acetoxy group. Specific examples of the 2-amino-6-substituted-purine include 2-amino-6-halogenopurine, 2,6-diaminopurine, 2-amino-6-hydroxypurine, 2-amino-6-chloropurine, 2-amino-6-iodopurine, 2-amino-6-mercaptopurine, 2-amino-6-methylmercaptopurine, 2-amino-6-hydroxyaminopurine, 2-amino-6-benzoylpurine, and 2-amino-6-acetoxypurine. Particularly, 2,6-diaminopurine is preferred.

No particular limitation is imposed on the hydrolase to be employed, so long as it has an activity capable of hydrolyzing the substituent at position 6 of the 2-amino-6-substituted-purine or a nucleoside having the purine, thereby producing 2-amino-6-oxopurine (guanine) or a nucleoside having the purine. Examples of such a hydrolase include deaminase. Particularly, adenosine deaminase is preferred.

Specifically, deamination reaction employing the hydrolase can be performed through addition of the hydrolase (about 5 units/mL or more, preferably about 30 units/mL or more) in a buffer solution such as a phosphate buffer solution or a Tris-HCl buffer solution. The reaction temperature is preferably 20 to 70° C., and the reaction time is preferably about 1 to about 100 hours. If desired, the reaction may be performed with stirring.

The deamination reaction employing the hydrolase may be performed subsequent to or simultaneously with the above-described reaction employing nucleoside phosphorylase.

The compound (VII) can also be produced by adding a nucleoside phosphorylase and a nucleosidase to the compound (I) or the αβ-isomers mixture (V') and to a guanosine 5'-monophosphate. The reaction can be performed through addition of the nucleoside phosphorylase and nucleosidase (about 5 units/mL or more each) in a buffer solution such as a Tris-HCl buffer solution or a phosphate buffer solution at 20 to 70° C. for about 1 to about 100 hours witk if desired, stirring.

The thus-produced compound (VII) may be isolated and purified through generally employed isolation/purification means for nucleoside, such as ion exchange chromatography, adsorption chromatography, or crystallization.

EXAMPLES

The present invention will next be described in more detail by way of synthesis examples, which should not be construed as limiting the invention thereto.

Synthesis Example 1

3,5-O-Dibenzoyl-2-fluoro-α-D-arabinosyl-1-phosphate [Formula V; $R^1$=Bz, $R^2$=H]

Phosphoric acid (5.0 g, 51 mmol) and molecular sieves 4A (3.6 g) were suspended in acetonitrile (18 mL), and tri-n-butylamine (24.3 mL, 102 mmol) was added to the resultant suspension at 0° C., followed by stirring at room temperature for one hour. Tetra-n-butylammonium iodide (15.7 g, 42.5 mmol) was added to the resultant mixture at room temperature, and 10 minutes later, an acetonitrile solution (36 mL) of 3,5-O-dibenzoyl-2-fluoro-α-D-arabinosyl-1-bromide [formula III; $R^1$=Bz, X=Br] (3.59 g, 8.5 mmol) was added dropwise thereto. After the resultant mixture was stirred at room temperature for two hours, insoluble matters were removed through filtration. The filtrate was concentrated under reduced pressure, and the resultant residue was subjected to extraction with ethyl acetate (150 mL). The organic layer was washed three times with 0.1 N hydrochloric acid, and then dried over anhydrous sodium sulfate, followed by removal of the solvent through evaporation.

The title compound was analyzed by means of HPLC [UV: 230 nm, analysis column: SHISEIDO CAPCELL PAK $NH_2$ (4.6 mm I.D.×250 mm), column temperature: 30° C., mobile phase: 60 mM $KH_2PO_4$ (50%)-acetonitrile (50%), pH 4.0 ($H_3PO_4$), flow rate: 1.0 mL/min], and the percent formation of the 1-phosphate derivative and the α/β ratio were calculated on the basis of area % (60.3%, α/β=3.4).

The above-obtained residue was dissolved in methyl ethyl ketone (90 mL), and phosphoric acid (13.3 g) and molecular sieves 4A (3.6 g) were added to the resultant solution, followed by stirring at 80° C. for two hours. After insoluble matters were removed through filtration, the solvent was removed through evaporation. The resultant residue was subjected to extraction with ethyl acetate (150 mL). The organic layer was washed with water, and then dried over anhydrous sodium sulfate, followed by removal of the solvent through evaporation. HPLC analysis: 60.5%, α/β=4.9.

The thus-obtained residue was further purified by means of reverse-phase ODS column chromatography (600 mL, 5 to 40% aqueous acetonitrile), to thereby yield 2.91 g (41%) of the title compound as a mixture with the β-isomer ($^{31}$P-NMR analysis: α/β=5.7) (which contains 0.6 mol of tri-n-butylammonium and 0.1 mol of tetra-n-butylammonium on the basis of 1 mol of the title compound).

$^1$H-NMR (CDCl$_3$, 500 MHz) δ ppm: 8.07-8.02 (4H, m), 7.51-7.36 (6H, m), 5.99 (1H, dd, J=5.6, 8.6 Hz), 5.46 (1H, dd, J=4.3, 22.9 Hz), 5.30 (1H, d, J=49.1 Hz), 4.74-4.57 (3H, m).

Synthesis Example 2

3,5-O-Dibenzoyl-2-fluoro-α-D-arabinosyl-1-phosphate [Formula V; $R^1$=Bz, $R^2$=H]

Molecular sieves 4A (50 mg) and a strong acid salt as shown below in Table 1 (0.6 mmol) were added to an acetonitrile solution (0.75 mL) of 1.0 M phosphoric acid/tri-n-butylamine, and the resultant mixture was stirred at room temperature for 40 minutes. To the mixture was added dropwise an acetonitrile solution (0.5 mL) of 3,5-O-dibenzoyl-2-fluoro-α-D-arabinosyl-1-bromide [formula III; $R^1$=Bz, X=Br] (50 mg, 0.12 mmol).

HPLC analysis (retention time): α-isomer (3.8 min), β-isomer (4.4 min).

The results are shown in Table 1. As is clear from Table 1, addition of a strong acid salt increases the α-isomer production ratio.

TABLE 1

| Strong acid salt | Reaction temperature | Compound (V) | α/β ratio |
|---|---|---|---|
| None | Room temp. | 68% | 0.6 |
| Tetra-n-butylammonium iodide | Room temp. | 69% | 2.4 |
| Tetra-n-butylammonium bromide | Room temp. | 69% | 2.2 |
| Tetra-n-butylammonium nitrate | Room temp. | 65% | 2.6 |
| Tetra-n-butylammonium chloride | 70° C. | 71% | 1.9 |
| Tetraethylammonium chloride | 70° C. | 65% | 1.9 |

Synthesis Example 3

3,5-O-Dibenzoyl-2-fluoro-α-D-arabinose [Formula IV; $R^1$=Bz]

3,5-O-Dibenzoyl-2-fluoro-α-D-arabinosyl-1-bromide [formula III; $R^1$=Bz, X=Br] (2.40 g, 5.7 mmol) was dissolved in DMF (50 mL), and triethylamine (4.8 mL, 34.2 mmol) and water (3.1 mL, 171 mmol) were added to the resultant solution, followed by stirring at room temperature for 30 minutes. The solvent was removed through evaporation under reduced pressure, and the resultant residue was subjected to extraction with ethyl acetate. The organic layer was washed with water, a saturated aqueous sodium hydrogencarbonate solution and a saturated aqueous sodium chloride solution. Subsequently, the organic layer was dried over anhydrous sodium sulfate, and then the solvent was removed through evaporation. The resultant residue was purified by means of silica gel column chromatography (150 g, 0 to 5% methanol-chloroform), to thereby yield 1.85 g (90%) of the title compound.

$^1$H-NMR (CDCl$_3$, 500 MHz) δ ppm: 8.08-8.01 (4H, m), 7.63-7.41 (6H, m), 5.70 (1H, dd, J=3.6, 10.2 Hz), 5.50 (1H, dd, J=4.3, 22.0 Hz), 5.18 (1H, d, J=49.1 Hz), 4.77-4.60 (3H, m), 2.89 (1H, t, J=3.4 Hz)

Synthesis Example 4

3,5-O-Dibenzoyl-2-fluoro-α-D-arabinosyl-1-(bis-2-cyanoethyl) phosphate [Formula V; $R^1$=Bz, $R^2$=CH$_2$CH$_2$CN]

3,5-O-Dibenzoyl-2-fluoro-α-D-arabinose [IV; $R^1$=Bz] (1.01 g, 2.8 mmol) was dehydrated through co-evaporation twice with acetonitrile, and then dissolved in acetonitrile (20 mL). Triethylamine (1.2 mL, 8.4 mmol) and bis(diisopropylamino)chlorophosphine (1.69 g, 5.6 mmol) were added to the resultant solution, followed by stirring at room temperature for one hour. 2-Cyanoethanol (1.9 mL, 28 mmol) and 1H-tetrazole (0.98 g, 14 mmol) were added to the resultant mixture, followed by stirring at room temperature for 1.5 hours. Subsequently, 70% t-butyl hydroperoxide solution (2.5 mL) was added to the resultant mixture, followed by stirring at room temperature for 30 minutes. The resultant mixture was subjected to extraction with ethyl acetate (100 mL), and the organic layer was washed with water (twice), an aqueous sodium thiosulfate solution (once), a saturated aqueous sodium hydrogencarbonate solution (once), and a saturated aqueous sodium chloride solution (once). The organic layer was dried over anhydrous sodium sulfate, and then the solvent was removed through evaporation under reduced pressure. The resultant residue was purified by means of silica gel column chromatography (70 g, 50 to 100% ethyl acetate-n-hexane), to thereby yield 0.78 g (51%) of the title compound.

$^1$H-NMR (CDCl$_3$, 500 MHz) δ ppm: 8.07-8.05 (4H, m), 7.65-7.43 (6H, m), 6.14 (1H, dd, J=4.2, 8.3 Hz), 5.56 (1H, dd, J=3.9, 20.9 Hz), 5.34 (1H, d, J=48.4 Hz), 4.82 (1H, q, J=3.9 Hz), 4.78 (1H, dd, J=3.5, 12.2 Hz), 4.68 (1H, dd, J=4.6, 12.2 Hz), 4.37-4.27 (4H, m), 2.78-2.68 (4H, m).

Synthesis Example 5

3,5-O-Dibenzoyl-2-fluoro-α-D-arabinosyl-1-phosphate [Formula V; $R^1$=Bz, $R^2$=H]

3,5-O-Dibenzoyl-2-fluoro-α-D-arabinosyl-1-(bis-2-cyanoethyl) phosphate [formula V; $R^1$=Bz, $R^2$=CH$_2$CH$_2$CN] (85 mg, 0.16 mmol) was dissolved in methylene chloride (3 mL), and DBU (0.25 mL, 1.6 mmol) was added to the resultant solution, followed by stirring at room temperature for 10 minutes. Chlorotrimethylsilane (0.1 mL, 0.8 mmol) was added to the resultant mixture, followed by stirring at room temperature for one hour. The resultant reaction mixture was subjected to extraction with chloroform, and the organic layer was washed with 0.1 N hydrochloric acid and then dried over anhydrous sodium sulfate. The resultant residue was dissolved in ethyl acetate (0.5 mL), and n-hexane (5 mL) was added dropwise to the resultant solution. The resultant supernatant liquid was removed, and the residue was dried under vacuum, to thereby yield 71 mg (89%) of the title compound (which contains 0.4 mol of DBU on the basis of 1 mol of the title compound).

$^1$H-NMR (CDCl$_3$, 500 MHz) δ ppm: 8.07-8.02 (4H, m), 7.51-7.36 (6H, m), 5.99 (1H, dd, J=5.6, 8.6 Hz), 5.46 (1H, dd, J=4.3, 22.9 Hz), 5.30 (1H, d, J=49.1 Hz), 4.74-4.57 (3H, m).

Synthesis Example 6

2-Fluoro-α-D-arabinosyl-1-phosphate disodium salt [Formula I]

The 3,5-O-dibenzoyl-2-fluoro-α-D-arabinosyl-1-(bis-2-cyanoethyl) phosphate [formula V; $R^1$=Bz, $R^2$=CH$_2$CH$_2$CN] synthesized in Synthesis Example 4 (590 mg, 1.08 mmol) was dissolved in methanol-THF (1:1, 6 mL), and 28% aqueous ammonia (6 mL) was added to the resultant solution, followed by stirring at room temperature for one hour. After the solvent was removed through evaporation, 28% aqueous ammonia (10 mL) was added to the resultant product, followed by stirring at room temperature overnight. The solvent was removed through evaporation, water (20 mL) was added to the resultant residue, and the resultant mixture was washed with ethyl acetate (20 mL). The aqueous layer was collected, and prepared into 100 mL of an aqueous solution. The aqueous solution was caused to pass through a cation-exchange resin (PK216, product of Mitsubishi Chemical Corporation, Na-type, 30 mL) for removal of water, to thereby yield 273 mg (99%) of the title compound.

$^1$H-NMR (D$_2$O, 500 MHz) δ ppm: 5.70 (1H, dd, J=6.9, 9.8 Hz), 5.02 (1H, d, J=50.5 Hz), 4.26-4.17 (2H, m), 3.87 (1H, dd, J=3.2, 12.4 Hz), 3.74 (1H, dd, J=5.3, 12.4 Hz).

Synthesis Example 7

2-Fluoro-α-D-arabinosyl-1-phosphate [Formula I]

The 3,5-O-dibenzoyl-2-fluoro-α-D-arabinosyl-1-phosphate [formula V; $R^1$=Bz, $R^2$=H] synthesized in Synthesis Example 1 (2.8 g, 3.38 mmol as the α-isomer) was dissolved in methanol (70 mL), and 28% aqueous ammonia (70 mL) was added to the resultant solution, followed by stirring at room temperature for 1.5 hours. Subsequently, 28% aqueous ammonia (70 mL) was added to the resultant mixture, followed by stirring at room temperature overnight. The solvent was removed through evaporation under reduced pressure, and the resultant residue was dissolved in water (50 mL). The resultant solution was washed twice with ethyl acetate (100 mL), and the aqueous layer was collected. The aqueous layer was concentrated under reduced pressure, and then the resultant concentrate was subjected to filtration by use of a membrane filter (PTFE, 0.45 μm), followed by concentration of the filtrate. Acetone (10 mL) was added twice to the resultant residue, and the supernatant liquid was removed. The resultant residue was co-evaporation twice with ethanol, and then dried under reduced pressure at 50° C. for two hours, to thereby yield 1.36 g of a crude product of the title compound.

$^1$H-NMR (D$_2$O, 500 MHz) δ ppm: 5.71 (1H, dd, J=6.9, 9.9 Hz), 5.02 (1H, d, J=50.3 Hz), 4.27-4.18 (2H, m), 3.88-3.71 (2H, m).

Synthesis Example 8

9-(2-Fluoro-β-D-arabinosyl)adenine [Formula II; B=adenine]

Molecular sieves 4A (126 mg) and tri-n-butylamine (0.67 mL, 2.8 mmol) were added to an acetonitrile solution (2.8 mL, 2.8 mmol) of 1.0 M phosphoric acid/tri-n-butylamine, followed by stirring at room temperature for one hour. Tetra-n-butylammonium iodide (0.87 g, 2.4 mmol) was added to the resultant mixture at room temperature, and 10 minutes later, an acetonitrile solution (2 mL) of 3,5-O-dibenzoyl-2-fluoro-α-D-arabinosyl-1-bromide [formula III; $R^1$=Bz, X=Br] (0.2 g, 0.47 mmol) was added dropwise thereto. After the resultant mixture was stirred at room temperature for two hours, insoluble matters were removed through filtration. The filtrate was concentrated under reduced pressure, and the resultant residue was subjected to extraction with ethyl acetate (20 mL). The organic layer was washed three times with 0.1 N hydrochloric acid, and then dried over anhydrous sodium sulfate, followed by removal of the solvent through evaporation. The resultant residue was dissolved in methyl ethyl ketone (5 mL), and phosphoric acid (0.74 g) and molecular sieves 4A (0.2 g) were added to the resultant solution, followed by stirring at 80° C. for three hours. After insoluble matters were removed through filtration, the solvent was removed through evaporation. The resultant residue was subjected to extraction with ethyl acetate (20 mL). The organic layer was washed with water, and then dried over anhydrous sodium sulfate, followed by removal of the solvent through evaporation, to thereby yield a crude product of the title compound (HPLC analysis: 56.4%, α/β=7.3).

The crude product was dissolved in methanol (4 mL), and 28% aqueous ammonia (2 mL) was added to the resultant solution, followed by stirring at room temperature for one hour. Subsequently, 28% aqueous ammonia (2 mL) was added to the resultant mixture, followed by stirring at room temperature overnight. The solvent was removed through evaporation under reduced pressure, and the resultant residue was dissolved in water (20 mL). The resultant solution was washed twice with ethyl acetate (50 mL), and the aqueous layer was collected. The aqueous layer was concentrated under reduced pressure, and the resultant residue was dissolved in 20 mM potassium phosphate buffer solution (20 mL, pH 7.6). Adenine (54 mg, 0.4 mmol) and purine nucleoside phosphorylase (crude enzyme, 1,750 units) were added to the resultant solution, and the resultant mixture was allowed to stand still at 50° C. for four days. The resultant reaction mixture was subjected to filtration by use of a membrane filter (PTFE, 0.45 μm), and the filtrate was prepared into 40 mL of an aqueous solution. Thereafter, the aqueous solution was purified by means of reverse-phase ODS column chromatography (40 mL, 0 to 5% acetonitrile-water), to thereby yield 50 mg of the title compound as colorless crystals (yield on the basis of adenine: 46%).

$^1$H-NMR (DMSO-$d_6$, 500 MHz) δ ppm: 8.26 (1H, d, J=1.7 Hz), 8.17 (1H, s), 7.36 (2H, brs), 6.41 (1H, dd, J=4.6, 14.1 Hz), 6.15 (1H, br), 5.25 (1H, br), 5.22 (1H, dt, J=4.3, 52.7 Hz), 4.47 (1H, dt, J=4.5, 19.4 Hz), 3.86-3.84 (1H,m), 3.68-3.63 (2H, m).

Synthesis Example 9

9-(2-Fluoro-β-D-arabinosyl)adenine [Formula II; B=adenine]

Phosphoric acid (2.8 g, 28.2 mmol) and molecular sieves 4A (2.0 g) were suspended in acetonitrile (10 mL), and tri-n-butylamine (13.4 mL, 56.4 mmol) was added to the resultant suspension at 0° C., followed by stirring at room temperature for one hour. Tetra-n-butylammonium iodide (8.7 g, 23.5 mmol) was added to the resultant mixture at room temperature, and 10 minutes later, an acetonitrile solution (20 mL) of 3,5-O-dibenzoyl-2-fluoro-α-D-arabinosyl-1-bromide [formula III; $R^1$=Bz, X=Br] (2.0 g, 4.7 mmol) was added dropwise thereto. After the resultant mixture was stirred at room temperature for two hours, insoluble matters were removed through filtration. The filtrate was concentrated under reduced pressure, and the resultant residue was subjected to extraction with ethyl acetate (150 mL). The organic layer was washed three times with 0.1 N hydrochloric acid, and then dried over anhydrous sodium sulfate, followed by removal of the solvent through evaporation. The resultant residue was dissolved in methyl ethyl ketone (50 mL), and phosphoric acid (7.4 g) and molecular sieves 4A (2.0 g) were added to the resultant solution, followed by stirring at 80° C. for two hours. After insoluble matters were removed through filtration, the solvent was removed through evaporation. The resultant residue was subjected to extraction with ethyl acetate (150 mL). The organic layer was washed with water, and then dried over anhydrous sodium sulfate, followed by removal of the solvent through evaporation (HPLC analysis: 67.4%, α/β=3.1).

The resultant product was dissolved in methanol (40 mL), and 28% aqueous ammonia (20 mL) was added to the resultant solution, followed by stirring at room temperature for one hour. Subsequently, 28% aqueous ammonia (20 mL) was added to the resultant mixture, followed by stirring at room temperature overnight. The solvent was removed through evaporation under reduced pressure, and the resultant residue was dissolved in water (50 mL). The resultant solution was washed twice with ethyl acetate (200 mL), and the aqueous layer was collected. The aqueous layer was concentrated under reduced pressure, to thereby yield a crude product of the title compound.

One half of the crude product of the title compound was dissolved in 20 mM potassium phosphate buffer solution (100 mL, pH 7.6). Adenine (270 mg, 2.0 mmol) and purine nucleoside phosphorylase (crude enzyme, 2,000 units) were added to the resultant solution, and the resultant mixture was allowed to stand still at 50° C. for six days. The resultant reaction mixture was subjected to filtration by use of a membrane filter (PTFE, 0.45 μm), and the filtrate was prepared into 150 mL of an aqueous solution. Thereafter, the aqueous solution was purified by means of reverse-phase ODS column chromatography (200 mL, 0 to 5% acetonitrile-water), to thereby yield 181 mg of the title compound as colorless crystals (yield on the basis of adenine: 34%).

$^1$H-NMR (DMSO-$d_6$, 500 MHz) δ ppm: 8.26 (1H, d, J=1.7 Hz), 8.17 (1H, s), 7.36 (2H, brs), 6.41 (1H, dd, J=4.6, 14.1 Hz), 6.15 (1H, br), 5.25 (1H, br), 5.22 (1H, dt, J=4.3, 52.7 Hz), 4.47 (1H, dt, J=4.5, 19.4 Hz), 3.86-3.84 (1H, m), 3.68-3.63 (2H, m).

Synthesis Example 10

2,6-Diamino-9-(2-fluoro-β-D-arabinosyl)purine [Formula II; B=2,6-diaminopurine]

One half of the crude 2-fluoro-α-D-arabinosyl-1-phosphate [formula I] obtained in Synthesis Example 9 was dissolved in 20 mM potassium phosphate buffer solution (100 mL, pH 7.6). 2,6-Diaminopurine (300 mg, 2.0 mmol) and purine nucleoside phosphorylase (crude enzyme, 2,000 units) were added to the resultant solution, and the resultant mixture was allowed to stand still at 50° C. for six days. The resultant reaction mixture was subjected to filtration by use of a membrane (PTFE, 0.45 mm), and the filtrate was prepared into 150 mL of an aqueous solution. Thereafter, the aqueous solution was purified by means of reverse-phase ODS column chromatography (200 mL, 0 to 3% acetonitrile-water), to thereby yield 228 mg of the title compound as colorless crystals (yield on the basis of 2,6-diaminopurine: 40%).

$^1$H-NMR (DMSO-$d_6$, 500 MHz) δ ppm: 7.81 (1H, d, J=2.4 Hz), 6.79 (2H, brs), 6.18 (1H, dd, J=4.2, 16.5 Hz), 5.89 (3H, brs), 5.20 (1H, br), 5.10 (1H, dt, J=3.7, 52.6 Hz), 4.39 (1H, ddd, J=3.7, 4.5, 18.2 Hz), 3.82-3.80 (1H, m), 3.79-3.60 (2H, m).

Synthesis Example 11

9-(2-Fluoro-β-D-arabinosyl)guanine [Formula II; B=guanine]

2,6-Diamino-9-(2-fluoro-β-D-arabinosyl)purine (61.2 mg, 0.21 mmol) was dissolved in 50 mM Tris-HCl buffer solution (20 mL, pH 7.0), and adenosine deaminase (71 units) was added to the resultant solution, followed by stirring at room temperature for 1.5 hours. The resultant reaction mixture was subjected to filtration by use of a membrane filter (PTFE, 0.5 μm), and the filtrate was prepared into 60 mL of an aqueous solution. The aqueous solution was purified by means of reverse-phase ODS column chromatography (80 mL, 0 to 2% aqueous acetonitrile), to thereby yield 60.4 mg of the title compound as colorless crystals (yield: 100%).

$^1$H-NMR (DMSO-$d_6$, 500 MHz) δ ppm: 10.50 (1H, brs), 7.80 (1H, s), 6.54 (2H, brs), 6.13 (1H, dd, J=4.2, 16.0 Hz), 5.94 (1H, d, J=4.5 Hz), 5.11 (1H, dt, J=3.8, 52.4 Hz), 5.08 (1H, t, J=5.7 Hz), 4.37 (1H, dd, J=3.9, 17.8 Hz), 3.82-3.79 (1H, m), 3.66-3.57 (2H, m).

Synthesis Example 12

2-Amino-6-chloro-9-(2-fluoro-β-D-arabinosyl)purine [Formula II; B=2-amino-6-chloropurine]

The crude 2-fluoro-α-D-arabinosyl-1-phosphate [formula I] obtained in Synthesis Example 7 (200 mg, 0.5 mmol) was dissolved in 50 mM potassium phosphate buffer solution (150 mL, pH 7.5). 2-Amino-6-chloropurine (170 mg, 1.0 mmol) and purine nucleoside phosphorylase (crude enzyme, 3,519 units) were added to the resultant solution, and the resultant mixture was allowed to stand still at 50° C. for 14 days. The resultant reaction mixture was subjected to filtration by use of a membrane filter (PTFE, 0.45 μm), and the filtrate was prepared into 10 mL of an aqueous solution. Thereafter, the aqueous solution was purified by means of reverse-phase ODS column chromatography (20 mL, 0 to 5% aqueous acetonitrile), to thereby yield the title compound.

$^1$H-NMR (D$_2$O, 500 MHz) δ ppm: 8.20 (1H, s), 6.31 (1H, dd, J=3.9, 17.4 Hz), 5.24 (1H, dt, J=3.1, 51.2 Hz), 4.56 (1H, dt, J=2.2, 18.2 Hz), 4.10-4.07 (1H, m), 3.92-3.82 (2H, m).

Synthesis Example 13

2-Amino-9-(2-fluoro-β-D-arabinosyl)purine [Formula II; B=2-aminopurine]

The crude 2-fluoro-α-D-arabinosyl-1-phosphate [formula I] obtained in Synthesis Example 7 (200 mg, 0.5 mmol) was dissolved in 50 mM potassium phosphate buffer solution (50 mL, pH 7.5). 2-Aminopurine (135 mg, 1.0 mmol) and purine nucleoside phosphorylase (crude enzyme, 1,517 units) were added to the resultant solution, and the resultant mixture was allowed to stand still at 50° C. for nine days. The resultant reaction mixture was subjected to filtration by use of a membrane filter (PTFE, 0.45 μm), and the filtrate was prepared into 6 mL of an aqueous solution. Thereafter, the aqueous solution was purified by means of reverse-phase ODS column chromatography (40 mL, 0 to 5% aqueous acetonitrile), to thereby yield 87.3 mg of the title compound (yield on the basis of 2-aminopurine: 32%).

$^1$H-NMR (DMSO-$d_6$, 500 MHz) δ ppm: 8.63 (1H, s), 8.18 (1H, d, J=2.2 Hz), 6.64 (2H, brs), 6.50 (1H, br), 6.31 (1H, dd, J=4.4, 15.2 Hz), 5.19 (1H, dt, J=4.1, 52.6 Hz), 5.15 (1H, br), 4.43 (1H, ddd, J=4.0, 4.9, 18.3 Hz), 3.85 (1H, q, J=4.9 Hz), 3.70-3.62 (2H, m).

Synthesis Example 14

2-Fluoro-9-(2-fluoro-β-D-arabinosyl)adenine [Formula II; B=2-fluoroadenine]

The crude 2-fluoro-α-D-arabinosyl-1-phosphate [formula I] obtained in Synthesis Example 7 (76 mg, 0.2 mmol) was dissolved in 5 mM Tris-HCl buffer solution (60 mL, pH 7.5). 2-Fluoroadenine (44 mg, 0.3 mmol) and purine nucleoside phosphorylase (crude enzyme, 722 units) were added to the resultant solution, and the resultant mixture was allowed to stand still at 50° C. for five days. The resultant reaction mixture was subjected to filtration by use of a membrane filter (PTFE, 0.45 μm), and the filtrate was prepared into 30 mL of an aqueous solution. Thereafter, the aqueous solution was purified by means of reverse-phase ODS column chromatography (40 mL, 0 to 5% aqueous acetonitrile), to thereby yield 39.0 mg of the title compound (yield on the basis of 2-fluoroadenine: 45%).

$^1$H-NMR (DMSO-$d_6$, 500 MHz) δ ppm: 8.24 (1H, d, J=1.9 Hz), 8.00-7.80 (2H, m), 6.29 (1H, dd, J=4.6, 13.8 Hz), 5.98 (1H, d, J=5.1 Hz), 5.22 (1H, dt, J=4.2, 52.6 Hz), 5.10 (1H, t, J=5.6 Hz), 4.43 (1H, ddd, J=5.0, 9.4, 18.9 Hz), 3.85 (1H, dd, J=4.9, 9.6 Hz), 3.71-3.61 (2H, m).

Synthesis Example 15

9-(2-Fluoro-β-D-arabinosyl)guanine [Formula II; B=guanine]

Phosphoric acid (48.1 g, 0.49 mol) and molecular sieves 4A (38 g) were suspended in acetonitrile (160 mL), and tri-n-butylamine (233.9 mL, 0.98 mol) was added to the resultant suspension at 0° C., followed by stirring at room temperature for one hour. Tetra-n-butylammonium iodide (151.0 g, 0.41 mol) was added to the resultant mixture at room temperature, and 10 minutes later, an acetonitrile solution (240 mL) of 3,5-O-dibenzoyl-2-fluoro-α-D-arabinosyl-1-bromide [formula III; R$^1$=Bz, X=Br] (34.62 g, 0.82 mol) was added dropwise thereto. After the resultant mixture was stirred at room temperature for two hours, insoluble matters were removed through filtration. The filtrate was concentrated under reduced pressure, water (200 mL) was added to the resultant residue, and the resultant mixture was subjected to extraction twice with ethyl acetate (600 mL). The organic layer was dried over anhydrous sodium sulfate, and the solvent was removed through evaporation. The resultant residue was dissolved in methyl ethyl ketone (830 mL), and phosphoric acid (110.6 g) was added to the resultant solution, followed by stirring at 80° C. for two hours. The solvent was removed through evaporation, water (1 L) was added to the resultant residue, and the resultant mixture was subjected to extraction twice with ethyl acetate (1 L). The organic layer was dried over anhydrous sodium sulfate, and then the solvent was removed through evaporation, to thereby yield crude 3,5-O-dibenzoyl-2-fluoro-α-D-arabinosyl-1-phosphate [formula V; R$^1$=Bz, R$^2$=H].

This crude compound was dissolved in methanol (600 mL), and 28% aqueous ammonia (300 mL) was added to the resultant solution, followed by stirring at room temperature for 1.5 hours. Subsequently, 28% aqueous ammonia (300 mL) was added to the resultant mixture, followed by stirring at room temperature overnight. The solvent was removed through evaporation under reduced pressure, and the resultant residue was dissolved in water (500 mL). The resultant solution was washed twice with ethyl acetate (800 mL), and the aqueous layer was collected. The aqueous layer was concentrated under reduced pressure, and then subjected to filtration by use of a membrane filter (PTFE, 0.45 μm). Thereafter, water was added to the filtrate, to thereby yield an aqueous solution of crude 2-fluoro-α-D-arabinosyl-1-phosphate [formula I] (2.5 L, pH 7.5).

2,6-Diaminopurine (15.4 g, 0.1 mol) and purine nucleoside phosphorylase (crude enzyme, 108,300 units) were added to the aqueous solution, and the resultant mixture was allowed to stand still at 50° C. for 10 days. The pH of the resultant reaction mixture was adjusted to 4 by use of dilute hydrochloric acid, and precipitates were removed through celite filtration. The filtrate was purified by use of an adsorption resin column (SP206, product of Mitsubishi Chemical Corporation, 1.4 L, 0 to 20% aqueous ethanol), and then concentrated, to thereby yield an aqueous solution of 2,6-diamino-9-(2-fluoro-β-D-arabinosyl)purine [formula II; B=2,6-diaminopurine] (3.1 L).

Sodium dihydrogenphosphate (8.4 g) was added to the aqueous solution, and the pH of the resultant mixture was adjusted to 7.3 by use of 1 N potassium hydroxide. Thereafter, adenosine deaminase (2,000 units) was added to the mixture, and the resultant mixture was allowed to stand still at 40° C. for three hours. The pH of the resultant reaction mixture was adjusted to 4 by use of dilute hydrochloric acid, and the mixture was purified by use of an adsorption resin column (SP206, product of Mitsubishi Chemical Corporation, 1.9 L, 0 to 15% aqueous ethanol), to thereby yield 7.8 g of the title compound as colorless crystals (HPLC purity: 99%, yield on the basis of 2,6-diaminopurine: 27%).

Reference Example 1

(1) Preparation of Purine Nucleoside Phosphorylase

*Escherichia coli* JM109 "pTrc-B56" carrying recombinant vector pTrc-B56 prepared through the method described in JP-A-H9-117298 was inoculated into a nutrition medium (100 mL) containing peptone (20 g/L), yeast extract (10 g/L), sodium chloride (5 g/L), glucose (1 g/L), and ampicillin (100 μg/mL), followed by shaking culture at 37° C.

At the time when bacterial cells reached a concentration of 4×10⁸ cells/mL, IPTG was added to the culture broth so as to attain a final concentration of 1 mmol/L, and shaking culture was further continued at 37° C. for five hours. After completion of culture, the cultured bacterial cells were collected through centrifugation (9,000×g, 10 minutes), and then suspended in 20 mL of a buffer solution (containing 50 mmol/L Tris-HCl buffer solution (pH 7.8), 5 mmol/L EDTA, and 0.1% Triton X100). Lysozyme was added to the bacterial cell suspension so as to attain a final concentration of 1 mg/mL, and the resultant suspension was maintained at 37° C. for one hour, to thereby induce bacteriolysis of the transformed bacterium. Subsequently, the bacterial cell residue was removed through centrifugation (12,000×g, 10 minutes). The thus-obtained supernatant fraction was employed as an enzyme.

(2) Preparation of Adenosine Deaminase

Transformed *Escherichia coli* JM105 [pDR-add] carrying recombinant vector pDR-add prepared through the method described in JP-A-H5-219978 was inoculated into a nutrition medium (100 mL) containing peptone (20 g/L), yeast extract (10 g/L), sodium chloride (5 g/L), glucose (1 g/L), and ampicillin (100 μmL), followed by shaking culture at 37° C.

At the time when bacterial cells reached a concentration of 4×10⁸ cells/mL, IPTG was added to the culture broth so as to attain a final concentration of 0.1 mmol/L, and shaking culture was further continued at 37° C. for three hours. After completion of culture, the cultured bacterial cells were collected through centrifugation (9,000×g, 10 minutes), and then suspended in 10 mL of a buffer solution (20 mmol/L Tris-HCl (pH 8.2), 10% ethylene glycol). The bacterial cell suspension was treated with an ultrasonic crusher, and subsequently the bacterial cell residue was removed through centrifugation (2,000×g, 10 minutes). The thus-obtained supernatant fraction was employed as an enzyme.

The invention claimed is:

1. α-1-Phosphorylated-2-deoxy-2-fluoroarabinoside represented by formula (I):

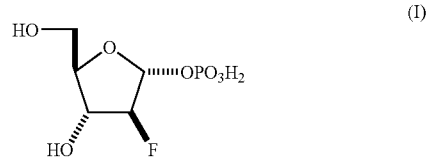

or a salt thereof.

2. A method for stereoselectively producing α-1-phosphorylated-2-deoxy-2-fluoroarabinoside represented by formula (I):

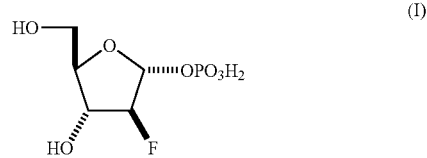

which method comprises hydrolyzing a 2-deoxy-2-fluoroarabinose derivative represented by formula (III):

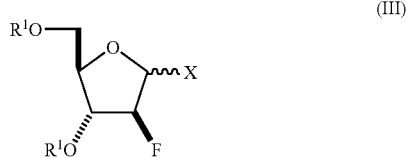

wherein $R^1$ represents a hydroxyl-protective group, and X represents a leaving group, thereby stereoselectively yielding an α-1-hydroxyl isomer represented by formula (IV):

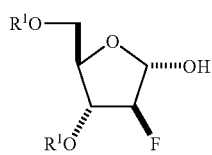

phosphorylating the compound of formula (IV), thereby forming an α-1-phosphorylated-2-deoxy-2-fluoroarabinoside derivative represented by formula (V):

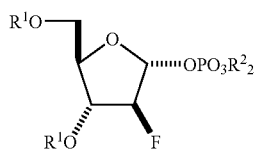

wherein $R^2$ represents a hydrogen atom or a phosphate-protective group; and subsequently removing the hydroxyl-protective group(s) and/or the phosphate-protective group(s).

3. A method for producing a mixture of α- and β-isomers of 1-phosphorylated-2-deoxy-2-fluoroarabinoside represented by formula (V'):

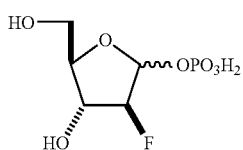

which method comprises phosphorylating, in the presence of a strong acid salt, a 2-deoxy-2-fluoroarabinose derivative represented by formula (III):

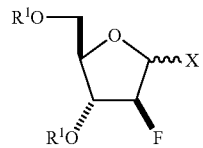

wherein $R^1$ represents a hydroxyl-protective group, and X represents a leaving group, thereby yielding a mixture of α- and β-isomers of a 1-phosphorylated-2-deoxy-2-fluoroarabinoside derivative represented by formula (V):

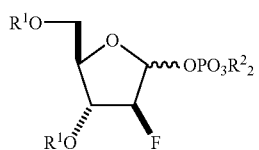

wherein $R^2$ represents a hydrogen atom or a phosphate-protective group; and subsequently removing the hydroxyl-protective group(s) and/or the phosphate-protective group(s).

4. A production method according to claim 3, wherein the strong acid salt employed generates a halide ion or a nitrate ion.

5. A method for producing 2'-deoxy-2'-fluoro-β-D-arabinonucleoside represented by formula (II):

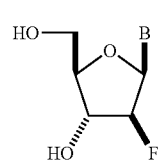

wherein B represents a base, which method comprises causing a nucleoside phosphorylase to act on α-1-phosphorylated-2-deoxy-2-fluoroarabinoside represented by formula (I):

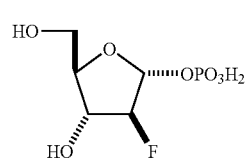

or a mixture of α- and β-isomers of 1-phosphorylated-2-deoxy-2-fluoroarabinoside represented by formula (V'):

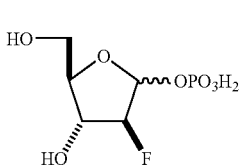

and on a base.

6. A production method according to claim 5, wherein the base is a purine base, or a purine base having a substituent selected from among a halogen atom, an alkyl group, a haloalkyl group, an alkenyl group, a haloalkenyl group, an alkynyl group, an amino group, an alkylamino group, a hydroxyl group, a hydroxyamino group, an aminooxy group, an alkoxy group, a mercapto group, an alkylmercapto group, an aryl group, an aryloxy group, and a cyano group.

7. A production method according to claim 5 or 6, wherein the nucleoside phosphorylase is purine nucleoside phosphorylase.

8. A method for producing 9-(2-fluoro-β-D-arabinosyl)guanine represented by formula (VII):

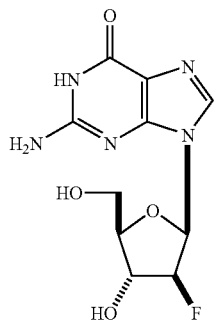

(VII)

which method comprises causing a nucleoside phosphorylase to act on α-1-phosphorylated-2-deoxy-2-fluoroarabinoside represented by formula (I):

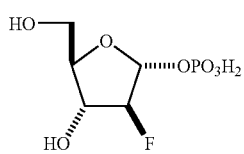

(I)

or a mixture of α- and β-isomers of 1-phosphorylated-2-deoxy-2-fluoroarabinoside represented by formula (V'):

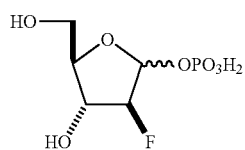

(V')

and on a 2-amino-6-substituted purine, thereby yielding 2-amino-6-substituted-9-(2-fluoro-β-D-arabinosyl)purine represented by formula (VI):

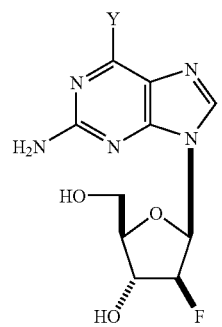

(VI)

wherein Y represents a substituent; and treating the thus-obtained purine nucleoside with a hydrolase.

9. A production method according to claim 8, wherein the 2-amino-6-substituted-purine is 2,6-diaminopurine.

10. A production method according to claim 8 or 9, wherein the hydrolase is deaminase.

11. A method for producing 9-(2-fluoro-β-D-arabinosyl) guanine represented by formula (VII):

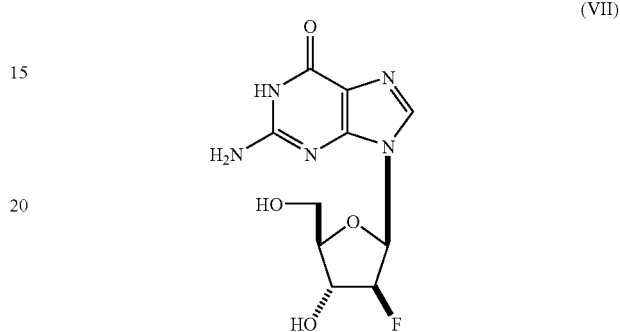

which method comprises causing a nucleoside phosphorylase and a nucleosidase to act on α-1-phosphorylated-2-deoxy-2-fluoroarabinoside represented by formula (I):

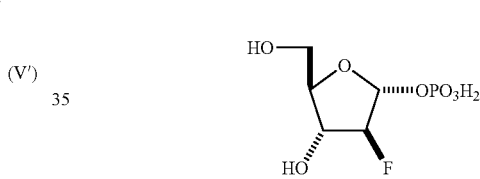

(I)

or a mixture of α- and β-isomers of 1-phosphorylated-2-deoxy-2-fluoroarabinoside represented by formula (V'):

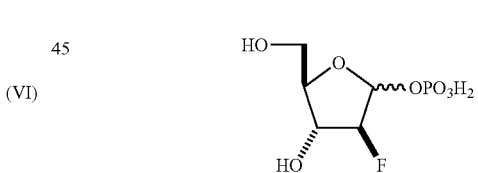

(V')

and on guanosine 5'-monophosphate.

12. A production method according to claim 11, wherein the nucleoside phosphorylase is purine nucleoside phosphorylase.

13. A production method according to claim 11 or 12, wherein the nucleosidase is inosinate nucleosidase.

* * * * *